United States Patent [19]

Kervennal et al.

[11] Patent Number: 4,650,899

[45] Date of Patent: Mar. 17, 1987

[54] LIQUID COMPOSITION CONTAINING DIISOCYANATE OF DIPHENYLURETHANE

[75] Inventors: Jacques Kervennal, Lyons; Henri Mathais, Saint-Didier-Au-Mont-D'Or; Raymond Commandeur, Vizille, all of France

[73] Assignee: Atochem, France

[21] Appl. No.: 603,964

[22] Filed: Apr. 26, 1984

[30] Foreign Application Priority Data

Apr. 29, 1983 [FR] France ................ 83 07116

[51] Int. Cl.$^4$ .......................................... C07C 119/048
[52] U.S. Cl. ................................ 560/359; 252/182; 560/347
[58] Field of Search ............ 260/453 AM, 453 PH; 564/331, 419; 560/359; 252/182

[56] References Cited

U.S. PATENT DOCUMENTS

| 3,149,162 | 9/1964 | Gardner et al. | 564/419 X |
| 3,362,979 | 1/1968 | Bentley | 260/453 AM |
| 3,676,497 | 7/1972 | Recchia | 260/453 AM |
| 4,118,411 | 10/1978 | Reiff et al. | 260/453 SP |

FOREIGN PATENT DOCUMENTS

| 0024665 | 8/1980 | European Pat. Off. . |
| 0046556 | 6/1981 | European Pat. Off. . |
| 0057862 | 1/1982 | European Pat. Off. . |
| 2930411 | 1/1981 | Fed. Rep. of Germany . |

*Primary Examiner*—Dolph H. Torrence
*Attorney, Agent, or Firm*—Sigalos & Levine

[57] ABSTRACT

A liquid composition comprising a mixture of isomers of essentially diisocyanates having the diphenylmethane structure, the distribution by weight of isomers in the composition for each 100 parts by weight of the composition being:

32 to 55% of the 4,4' isomer,
30 to 45% of the 2,4' isomer,
5 to 12% of the 3,4' isomer,
4 to 10% of the 2,2' isomer, and
2 to 5% of the 2,3' isomer;

and the method of making the composition by first reacting a benzyl halide with benzene, followed by nitration, hydrogenation, and phosgenation.

2 Claims, No Drawings

4,650,899

LIQUID COMPOSITION CONTAINING DIISOCYANATE OF DIPHENYLURETHANE

BACKGROUND OF THE INVENTION

The invention concerns a new liquid composition containing diisocyanates having a diphenylmethane structure obtained by the initial reaction of a benzyl halide with benzene, followed by a nitration of the aromatic rings, a hydrogenation and a phosgenation. The composition can be used to produce polyurethanes.

Some diisocyanates of diphenylmethane aromatic hydrocarbon structure (M.D.I.) are already being synthesized industrially and they are obtained by the condensation of two molecules of aniline with one of formaldehyde in the presence of an acid catalyst, followed by a phosgenation, leading to mixtures containing 4,4',2,4', and 2,2' isomers. But this condensation is never totally selective in 2-ring products and a mixture of polyisocyanates and diisocyanates is usually synthesized with the latter being separated by distillation in order to yield pure M.D.I. The 4,4' M.D.I. isomer generally is present in the largest amount and possesses a melting point of 38° C. Thus, depending on its concentration, it may be necessary to liquefy the mixture of diisocyanates before being able to use it, either by melting it or by transforming it chemically. Moreover, such solid mixtures do not stand storage very well and must be preserved in a cold chamber.

SUMMARY OF THE INVENTION

The compositions according to the invention have the advantage of being liquid at ordinary room temperature, which renders them directly utilizable, and, moreover, they keep well in storage. Furthermore, the benzyl portion of the diphenylmethane originates from toluene, a raw material which is less expensive than benzene and represents a noteworthy economic savings.

Briefly, the present invention comprises a liquid composition comprising a mixture of diisocyanate isomers having the diphenylmethane structure and being present, for each 100 parts by weight of the composition, in the following amounts by weight:
32 to 55% of the 4,4' isomer
30 to 45% of the 2,4' isomer,
5 to 12% of the 3,4' isomer,
4 to 10% of the 2,2' isomer, and
2 to 5% of the 2,3' isomer.

The invention also comprises the method of making such composition by first reacting a benzyl halide with benzene, nitrating the aromatic rings of the resultant reaction products, hydrogenating the dinitrated reaction products to the corresponding diamines, and phosgenating the amines to the corresponding diisocyanates.

DETAILED DESCRIPTION

The synthesis of isocyanates according to the invention calls for three successive reaction stages starting from diphenylmethane: one of nitration of the aromatic rings, one of hydrogenation, and one of phosgenation. The diphenylmethane utilized as the raw material can be prepared by controlled photochemical halogenation of toluene to form a benzyl halide which is condensed by FRIEDEL-CRAFTS reaction with an excess of benzene. Depending on the operating conditions and the catalyst used, by regulating the excess of benzene, good yields of diphenylmethane are obtained, but condensation products with 3 or 4 rings and more are also formed which can be separated by a distillation. However, the crude mixture can also be nitrated, then hydrogenated and phosgenated without prior separation. Thus, a mixture of diisocyanates and polyisocyanates is obtained, which can be used as is for certain applications of polyurethanes, but which can also be distilled in order to extract the diaryl isomers therefrom.

For the nitration, a mixture of nitric acid and sulfuric acid concentrated to at least 90% by weight is used. The nitric acid can be used in stoichiometrical quantities in relation to the aromatic compound, thus using one mole of acid per aromatic ring to be nitrated. It is, however, advantageous to operate in the presence of an excess of nitric acid; up to 20% in excess of the stoichiometric amount. The sulfuric acid can be used in equimolar quantities in relation to the nitric acid, but it can also be used in excess or in less than equimolar quantities. The nitration reaction can take place between 0° C. and the boiling temperature of the mixtures; usually between 0° C. and 50° C., with the aromatic compound preferably being rendered soluble in a solvent such as methylene chloride. The addition of the mixture of acids can thus take place at 0° C., but it is not inconvenient to operate at ambient temperature provided that the exothermicity of the reaction is controlled. The latter can take its course at ambient temperature, but it is preferable to operate with refluxing of the mixture, making it possible to partly eliminate the excess of nitric acid. The upper organic phase is then separated from the acids, neutralized, and evaporated to dryness. It is preferred to operate under nitrogen atmosphere, in a reactor equipped with efficient means of agitation and of temperature regulation.

By following the thus described operating method from pure diphenylmethane there is thus obtained products formed essentially of dinitration isomers containing from 32 to 55% of 4,4'-dinitro diphenylmethane, from 30 to 45% of the 2,4' isomer, from 5 to 12% of the 3,4' isomer, from 4 to 10% of the 2,2' isomer, and from 2 to 5% of the 2,3' isomer. Under identical conditions, the nitration of a mixture of diphenylmethane and of higher homologs leads to the corresponding nitrated products.

The second stage comprises the hydrogenation of the nitro derivatives into the corresponding amines. While it can be done chemically, it is preferable to operate under hydrogen pressure, in a pressure-resistant reactor equipped with agitation means and possessing conventional means of control and regulation, in the presence of a catalyst based on nickel, palladium, platinum, ruthenium, and others.

In this case, a hydrogenation reactor is used which makes it possible to work under pressures capable of reaching 100 bars. The reaction can take place without solvent at a temperature at which the nitro derivative is molten, or in conventional hydrogenation solvents such as alcohols, dioxane, ethers of ethylene glycol, and others.

It is preferred to use a catalyst constituted of palladium deposited on a support at concentrations between 1 and 10%, making it possible to operate at temperatures between 30° and 100° C. and pressures of 20 to 50 bars. The molar ratio of nitro derivatives/palladium is not imperatively fixed, but is preferably between 200 and 3,000. After reaction and filtration of the catalyst, the solvent if used is evaporated and the mixture of amines obtained can be used as is. It is also possible to separate the isomers of diamino-diphenylmethane at this stage by distillation.

The third stage calls for classical phosgenation techniques in a reactor equipped with agitation means and topped by a refrigerant. For instance, the mixture of amines is placed at a concentration of 5 to 20% into a chlorinated aromatic solvent such as monochlorobenzene or orthodichlorobenzene containing the required quantity of phosgene by maintaining the temperature in the vicinity of 20° C. The suspension is then progressively heated. The reaction mixture homogenizes at about 100° C. The temperature is slowly raised to the boiling point of the mixture and then the solvent is distilled in such a way as to recover the isocyanates having been formed.

The mixture can be used as is, for instance, in certain formulations for polyurethanes. However, the isomers of diisocyanates of diphenylmethane can be recovered by distillation under a high vacuum. Another technique consists of simultaneously introducing into the reactor a solution of diamine isomers in a chlorinated aromatic solvent and a stream of gaseous phosgene. The reaction can take place first at ordinary room temperature, and then the reactor is progressively heated as previously. However, the reaction can also be carried out directly in the vicinity of 100° C. and the formation of isocyanate then is practically immediate.

The isocyanates thus obtained can be used to produce, using the known and conventional techniques, polyurethanes possessing favorable properties.

In the examples that follow, the nitro derivatives have been analyzed by gas chromatography by using a Pyrex column having an internal and external diameter of 3 and 6 mm, respectively, and a length of 2 meters, filled with phase SP 2250 impregnated at 3% on a support of "Supelcoport" 100–120 mesh (SUPELCO) on which linear temperature programmings at 4° C./mn have been carried out from 180° C. to 280° C. The principal dinitro isomers have been synthesized pure or isolated by trapping and identified by nuclear magnetic resonance of $^{13}C$ and $^{1}H$.

For the amines, likewise analyzed by gas chromatography, there is used a 2-meter glass column, filled with chromosorb support W.N.A.W., 60–80 mesh, (JOHNS MANVILLE), impregnated at 5% of KOH and 5% of "Apiezon N" (Apiezon Products Limited) by operating isothermally at 220° C. The concentration of total amine functional groups is determined chemically. The NCO functional groups of the isocyanates are evaluated by chemical analysis, while the isomer compositions are determined by gas chromatography on the column and under the conditions used for the nitro derivatives. In the case in which crude mixtures are used which, outside of diphenylmethane, contain higher homologs, the corresponding nitro derivatives, aminated derivatives, and phosgenated derivatives are analyzed by gel permeation chromatography by using a SHODEX A-802 column.

The invention will be further described in connection with the examples which follow which are set forth for purposes of illustration only.

EXAMPLE 1

16.8 g of pure diphenylmethane (0.1 mole), prepared by FRIEDEL-CRAFTS condensation of benzyl chloride and benzene in excess and distilled, are dissolved in 40 ml of methylene chloride, and then a mixture of 14.1 g of 98.5% nitric acid and of 20 ml of 96% sulfuric acid is added dropwise in a half hour, while maintaining the temperature below 25° C. As soon as the addition is finished, the temperature is raised to refluxing for 3½ hours, and then cooling takes place. Two phases separate; the lower acid phase and the other upper organic phase. The organic phase is extracted and the acid phase washed twice with methylene chloride. The different organic phases are combined, neutralized with potassium carbonate, and the solvent is evaporated. After crushing, 24.5 g of a yellow powder are recovered, having a melting point of 154° C. and containing 99.3% of dinitration isomers of a composition of 48.3% of the 4,4' isomer, 33.2% of the 2,4' isomer, 8.2% of the 3.4' isomer, 6.3% of the 2,2' isomer, and 3% of the 2,3' isomer.

20 g of this mixture of isomers of dinitrodiphenylmethane are placed into the autoclave and 0.2 liters of methanol are added as well as 0.2 g of catalyst consisting of palladium deposited on carbon at 5%. After having flushed the reactor with nitrogen, 40 bars of hydrogen are introduced and heating takes place with agitation up to 70° C. After .1 hour of reaction time, the set-up is allowed to cool and decompressed and the reaction mixture is recovered, which is filtered in order to eliminate the catalyst. The methanol is evaporated to dryness and 15 g of isomers of diaminodiphenylmethane are obtained. 14 g of the latter are dissolved in 50 ml of orthodichlorobenzene, and the solution is introduced dropwise by means of a drip bulb into a reactor containing 38 g of phosgene in a foot of 50 ml of the same solvent, and maintained at 20° C. The reaction is allowed to take place for one-half hour at 20°–25° C. A greyish-white precipitate is formed immediately.

Heating then takes place at 45° C. for 1 hour, then 1 hour at 60° C. and one-half hour at 100° C. The mixture homogenizes and the temperature is raised to 140° C. for 2 hours while causing a stream of nitrogen to pass through the setup in order to expel the excess phosgene and the hydrochloric acid that is formed. Then the solvent is evaporated in vacuo, and 17.5 g of a mixture of isocyanates are collected whose distillation leads to a clear yellow liquid consisting of a mixture of isomers of diisocyanates of diphenylmethane (NCO content: 2 equivalents per mole); the total composition corresponding to the object of the present invention: 44.5% of the 4,4' isomer, 36.7% of the 2,4' isomer, 7.7% of the 3,4' isomer, 7% of the 2,2' isomer, and 3.2% of the 2,3' isomer.

EXAMPLE 2 (COMPARATIVE)

16.8 g of diphenylmethane are dissolved in 40 ml of methylene chloride. Operation takes place as in Example 1, but by using 17 g of 85% nitric acid and 30 g of 85% sulfuric acid. Refluxing is allowed to take place for 3½ hours, and then the organic phase is extracted and neutralized. Evaporation of the solvent leads to 22.5 g of a yellow product melting at 136° C. and containing 7.7% of diphenylmethane not having reacted, 1.3% of benzophenone resulting from an oxidation, 17.2% of mononitration isomers and 72.4% of the expected dinitration isomers. It is obvious that such a mixture no longer is advantageous within the scope of the present invention.

EXAMPLE 3 (COMPARATIVE)

Dinitrodiphenylmethane is prepared according to the operating method described in example 1 from 201.6 g of diphenylmethane by using 176 g of 98.7% nitric acid and 240 ml of 96% sulfuric acid. 40.7 g are removed therefrom and washed twice with 200 ml of ether in order to totally eliminate the 2,2' and 2,3' isomers from the mixture. After drying, 24.2 g of a white precipitate are recovered on the filter having a melting point of 158° C. and the following composition: 68% of 4,4'-dinitrodiphenylmethane, 29% of 2,4'-dinitrodiphenylmethane, and 3% of 3,4'-dinitrodiphenylmethane.

20 g of this mixture are hydrogenated under the conditions of Example 1, after distillation of the solvent leading to 15.3 g of diamines appearing in a viscous form of very light orange color.

After distillation of the mixture of isomers, the phosgenation of 15 g of this product yields 16.3 g of diisocyanates in the composition corresponding to the dinitro derivatives noted above (NCO content: 2 equivalents per mole). The melting point of this mixture is then 33° C. In this case, the property of being liquid, which the composition of the present invention containing the combination of isomers possesses, is lost.

EXAMPLE 4

In 50 ml of methylene chloride there are dissolved 20 g of a mixture obtained by the FRIEDEL-CRAFTS condensation of benzylchloride and benzene in the presence of FeCl3, with this mixture containing 43% of diphenylmethane, 24% of triaryl derivatives and 18% of compounds having 5 or more rings. 16.7 g of 98.7% nitric acid and 30.9 g of 96% sulfuric acid are added dropwise in 30 minutes, while limiting the temperature to below 25° C.

Refluxing is allowed to take place for 3½ hours, and then the organic phase is extracted and neutralized. After evaporation of the solvent, there is obtained 28.5 g of a mixture of nitro derivatives whose nitrogen content is 10.7% and whose distribution in aromatic rings analyzed by gel permeation chromatography is identical to the distribution of the starting product. 17 g of this mixture is hydrogenated in 0.2 l of methanol, in the presence of 0.2 g of palladium at 5% on carbon. After filtration of the catalyst and evaporation of the solvent, there is recovered 13 g of a viscous mixture of amines which can be caused to flow from 70° C. and up.

10 g of this mixture of amines are phosgenated in 100 ml of ortho-dichlorobenzene in the presence of 28 g of liquid phosgene by operating in the manner described in Example 1. After filtration and evaporation of the solvent we recover 11.6 g of a liquid mixture of isocyanates (NCO content: 6.86 functional groups per kg) containing isomers of diisocyanates of diphenylmethane of the following distribution: 49% of the 4,4' isomer, 34.1% of the 2,4' isomer, 7.8% of the 3,4' isomer, 6.1% of the 2,2'isomer, and 2o of the 2,3'isomer.

Furthermore, by distilling this crude product which can, however, be used as is, there is obtained a liquid mixture of the diisocyanate isomers of diphenylmethane, whose NCO content is 2 equivalents per mole, having a composition of 40% of the 4,4' isomer, 42% of the 2,4' isomer, 5.7% of the 3,4' isomer, 8.7% of the 2,2 isomer, and 3.2% of the 2,3' isomer.

EXAMPLE 5

17.7 g of a hydrocarbon mixture resulting from the FRIEDEL-CRAFTS condensation of benzyl chloride and benzene and containing 95% diphenyl methane and 4.5% triaryl derivatives are dissolved in 80 ml of methylene chloride and a mixture of 14.7 g of 98.7% nitric acid and 21.5 g of 95% sulfuric acid is added dropwise, while keeping the temperature below 25° C.

Refluxing is allowed to take place for 3½ hours and then the organic phase is extracted and neutralized. After evaporation of the solvent, there is obtained 27 g of a light yellow, slightly pastry product containing dinitrodiphenylmethane isomers having the following distribution: 44.2% of the 4,4' isomer, 35.5% of the 2,4' isomer, 8.8% of the 2,2' isomer, 7.9% of the 3,4' isomer, and 3.5% of the 2,3' isomer.

20 g of this mixture are hydrogenated in 200 ml of methanol in the presence of 0.2 g of palladium catalyst at 5% on carbon. After filtratin of the catalyst and evaporation of the solvent, 15 g of the amine mixture are recovered.

10 g of this mixture are solubilized in 50 ml of ortho-dichlorobenzene (ODCB), filtered, and introduced during 1 hour into a reactor containing 50 ml of ODCB at 80° C., while simultaneously admitting a gaseous stream of phosgene of 2.5 l/h. The reaction is allowed to proceed for 1 hour and then the temperature is allowed to rise to 100° C. for 1 hour, then to 140° C., at which temperature the phosgene stream is stopped in order to flush with nitrogen for 2 hours. The solvent is distilled and 11.3 g of a liquid mixture of isocyanates is recovered (NCO content: 7.7 equivalents per kg) in which the distribution of diphenylmethane diisocyanate isomers is in the vicinity of 43.3% of the 4,4' isomer, 37.1% of the 2,4' isomer, 8.4% of the 2,2' isomer, 7.7% of the 3,4' isomer, and 3.6% of the 2,3' isomer.

EXAMPLE 6

20 g of a hydrocarbon mixture resulting from the FRIEDEL-CRAFTS condensation of benzyl chloride and benzene and containing 67% of diphenylmethane, 20% of triaryl derivatives, 9% of tetraaryl derivatives, and 4% of pentaaryl derivatives and higher homologs are dissolved in 80 ml of methylene chloride and a mixture of 16.8 g of 98.7% nitric acid and 31.3 g of 96% sulfuric acid is poured in dropwise, while keeping the temperature below 25° C.

Refluxing is allowed to proceed for 3½ hours and then the organic phase is extracted and neutralized. After evaporation of the solvent, there is obtained 30 g of a mixture of nitro derivatives of maroon color and containing dinitrodiphenylmethane isomers having the following distribution: 48.2% of the 4,4' isomer, 33.6% of the 2,4' isomer, 8.4% of the 3,4' isomer, 6.5% of the 2,2' isomer, and 3.2% of the 2,3' isomer.

21 g of this mixture are hydrogenated in 200 ml of methanol in the presence of 0.2 g of palladium catalyst at 5% on carbon. After filtration of the catalyst and evaporation of the solvent, 16.2 g of the amine mixture are recovered.

10 g of this mixture are solubilized in 50 ml of ortho-dichlorobenzene (ODCB), filtered, and introduced in 1 hour into a reactor containing 50 ml of ODCB at 80° C., while simultaneously admitting a gaseous stream of phosgene of 3.1 l/h. By operating as in Example 5, there is recovered 11.8 g of a liquid mixture of isocyanates (NCO content: 7.69 equivalents per kg) in which the distribution of -the diphenylmethane diisocyanate isomers is close to 47.3% of the 4,4' isomer, 35% of the 2,4' isomer, 7.5% of the 3,4' isomer, 6.9% of the 2,2' isomer, and 3.2% of the 2,3'isomer.

EXAMPLE 7

A prepolymer is formed by causing distilled MDI, having been prepared in the same manner as in Example 1 (NCO content: 2 equivalents/mole), to react with a polypropyleneglycol of a molecular weight of 2000 ("UGIPOL" 1020) having previously been dehydrated. The amount of MDI is such that NCO/OH=2.05. A comparative test is carried out with commercial MDI - 4,4' in flakes and the results were as follows:

|  | MDI of the Invention | Commercial MDI - 4,4' |
|---|---|---|
| Reaction duration for a 100% conversion | 6 hours | 12 hours |
| Titer | 0.85 NCO/kg | 0.84 NCO/kg |
| Viscosity (25° C.) in cps | 34,400 | 35,000 |
| Appearance | transparent | opaque |

EXAMPLE 8

Specimens of elastomers were synthesized from distilled MDI prepared in the same manner as in Example 1 (NCO content: 8 equivalents/kg) and from liquid commercial MDI partially modified by carbodiimides and having a titer of 6.8 NCO/kg.

Implementation in the form of cast plates is done from butane diol polyadipate (molecular weight of 2000), 1,4-butanediol and MDI.

The polyadipate and the butanediol (previously dehydrated under vacuo for 1 hour at 80° C.) are mixed and then the MDI is added at 40° C. The mixture is degassed under vacuo and as soon as the temperature reaches 55°-60° C., the elastomer formed is run into a mold. Baking takes place for about 24 hours at 100° C. The results are summarized in the table below:

| MDI | According to the Invention | Commercial | According to the Invention | Commercial |
|---|---|---|---|---|
| 1,4-butanediol content (% by weight) | 10 | 10 | 20 | 20 |
| Appearance of the elastomer | Translucent | Opaque | Translucent | Opaque |
| Shore A Hardness | 77 | 82 | 62 | 89 |
| Tensile Strength Breaking Load (kgf/cm$^2$) | 339 | 377 | 424 | 480 |
| Elongation (%) | 446 | 407 | 642 | 275 |

While the invention has been described in connection with a preferred embodiment, it is not intended to limit the scope of the invention to the particular form set forth, but, on the contrary, it is intended to cover such alternatives, modifications, and equivalents as may be included in the spirit and scope of the invention as defined by the appended claims.

What is claimed is:

1. A liquid composition consisting essentially of a mixture of diisocyanate isomers having the diphenylmethane structure and containing by weight for each 100 parts by weight thereof about:

32 to 55% of the 4,4' isomer,
30 to 45% of the 2,4' isomer,
5 to 12% of the 3,4' isomer,
4 to 10% of the 2,2' isomer, and
2 to 5% of the 2,3' isomer.

2. The composition of claim 1 consisting essentially of:

40 to 49% of the 4,4' isomer,
36.7 to 42% of the 2,4' isomer,
5.7 to 7.7% of the 3,4' isomer,
7.0 to 8.7% of the 2,2' isomer, and
3.2% of the 2,3' isomer.

* * * * *